United States Patent
Dascalu

(12) 
(10) Patent No.: US 7,166,300 B1
(45) Date of Patent: Jan. 23, 2007

(54) AGENT FOR INDUCING HAIR GROWTH CONTAINING EXTRACTS OF SAW PALMETTO AND SWERTIA

(75) Inventor: Avi Dascalu, Tel-Aviv (IL)

(73) Assignee: Medidermis Ltd., Netanya (IL)

( * ) Notice: Subject to any disclaimer, the term of this patent is extended or adjusted under 35 U.S.C. 154(b) by 77 days.

(21) Appl. No.: 10/111,659

(22) PCT Filed: Oct. 19, 2000

(86) PCT No.: PCT/IL00/00660

§ 371 (c)(1),
(2), (4) Date: Apr. 25, 2002

(87) PCT Pub. No.: WO01/30311

PCT Pub. Date: May 3, 2001

(30) Foreign Application Priority Data

Oct. 28, 1999 (IL) .................................... 132625

(51) Int. Cl.
  A61K 9/14 (2006.01)
  A61K 9/20 (2006.01)
  A61K 9/48 (2006.01)
  A61K 9/66 (2006.01)

(52) U.S. Cl. ...................... 424/464; 424/451; 424/455; 424/489

(58) Field of Classification Search ............. 424/78.06, 424/78.07, 78.03, 71, 20, 70.1, 74, 401
See application file for complete search history.

(56) References Cited

U.S. PATENT DOCUMENTS

| | | | |
|---|---|---|---|
| 4,596,812 A | 6/1986 | Chidsey, III et al. | |
| 4,760,071 A | 7/1988 | Rasmusson et al. | |
| 4,769,231 A | 9/1988 | Ogura et al. | |
| 5,750,107 A | 5/1998 | Nomura | |
| 5,972,345 A * | 10/1999 | Chizick et al. | 424/727 |
| 6,419,913 B1 * | 7/2002 | Niemiec et al. | 424/78.07 |
| 2004/0110650 A1 * | 6/2004 | Siddiqui et al. | 510/119 |
| 2004/0171693 A1 * | 9/2004 | Gan et al. | 514/565 |

FOREIGN PATENT DOCUMENTS

| | | |
|---|---|---|
| EP | 0 584 365 B1 | 3/1994 |
| EP | 0 640 333 A2 | 3/1995 |
| EP | 0640333 A2 * | 3/1995 |
| JP | 63 275514 A | 11/1988 |
| JP | 63 303913 A | 12/1988 |
| JP | 09 100220 A | 4/1997 |
| JP | 409100220 A * | 4/1997 |
| WO | WO 9702041 A1 * | 1/1997 |

OTHER PUBLICATIONS

Great American Products, "Hair Maximizer Solutions Program", pp. 1-3.*
*Effect of Retinoids on Follicular Cells*, G. Bazzano et al., Journal of Investigative Dermatology, vol. 101, No. 1 Supp., Jul. 1993, pp. 138S-142S.
*Studies on Active Substances in Herbs Used for Hair Treatment. I. Effects of Herb Extracts on Hair Growth and Isolation of an Active Substance from Polyporus umbellatus F.*, Y. Inaoka et al., Chem. Phar. Bull. vol. 42, No. 3, 1994, pp. 530-533.
*Topical Minoxidil Therapy for Androgenetic Alopecia*, J. A. Koperski et al., Arch Dermtol, vol. 123, Nov. 1987, pp. 1483-1487.
SULTAN, *Inhibition Of Androgen Metabolism And Binding By A Liposterolic Extract Of "Serenoa Repens B" In Human Foreskin Fibroblasts*, J. Steroid Biochem, Jan. 10, 1984, 515, 1.

* cited by examiner

*Primary Examiner*—S. Tran
(74) *Attorney, Agent, or Firm*—Alston & Bird LLP

(57) ABSTRACT

The present invention consists in a composition comprising a mixture of extracts of saw palmetto and *swertia*, of derivatives thereof and of active components being part of said extracts. The composition may comprise additional agents and/or extracts, for example, irritating agents, extracts for hair invigoration, hair nourishment agents, anti-dandruff antiproliferative compounds, extracts with an antimicrobial, extracts with an antifungal, extracts with anti-inflammatory agents, extracts with a steroid, extracts with a nitric oxide donor and extracts with minoxidil. The concentration of the saw palmetto extract in the composition is suitably 0.01–100%. The composition may comprise a suitable carrier, solvent and/or emulgent. The composition may be, for example, an internally ingested tablet, a capsule, drops or a suspension. The invention relates also to the use of said composition in the preparation of a mixture for the application to humans and animals against the loss of hair and to method for the treatment with said composition for the treatment of humans and animals against loss of hair.

19 Claims, 1 Drawing Sheet

AGENT FOR INDUCING HAIR GROWTH CONTAINING EXTRACTS OF SAW PALMETTO AND SWERTIA

The present invention relates to plant extracts useful as modulators of hair growth during conditions of hair loss.

Normal scalp hair loss can be caused either by a physiologic pattern of aging or to a genetically controlled trend of non-scarring hair loss, named androgenetic alopecia. The hair loss of aging evolves as a slow process in middle-aged and elderly subjects, as a generally diffuse gradual and progressive hair thinning and loss from most of the hairy scalp. Contrary to the previous etiology, androgenetic alopecia develops earlier, even in 18 years old subjects, develops rapidly and involves specific temporal hair loss in male type, or vertex hair loss of female type androgenetic alopecia. In addition to the physiologic hair loss, various etiologies may cause hair deprivation, e.g. immune diseases (alopecia areata), pharmacological drugs (heparin, lithium) or diseases (fungal).

Generally, the hair follicle and resulting hair shaft are in continuous growth and involution, and develop in three general stages: anagen, the growth phase of about 3 years, catagen, a transitional 3 weeks phase of development preceding the catagen phase, an involution of the hair follicle lasting about 3 months, afterwards the hair starts its cycle again.

Various treatments were suggested for hair loss, such as
i) Topical minoxidil (U.S. Pat. No. 4,596,812) at concentrations from 1–5%, with an improvement in hair loss in about ⅓–⅔ of patients (Koperski et al, 1987). At the more effective higher concentrations, it cannot be used in women and may cause hypotension or hypertrichosis.
ii) A relatively new indication for the antiprostatic drug Finasteride (U.S. Pat. No. 4,760,071), improves hair loss after at least one-year daily uptake of the drug. Claims a 60% success as compared with 39% hair growth in control group, but without broad clinical evidence of efficacy and side effects, i.e. impotence.
iii) A variety of plant extracts were proposed as hair growths stimulants. Most of the data has not published in peer reviewed medical literature. Part of it is referred in various patents, e.g. U.S. Pat. Nos. 5,750,107 and 4,769,231, and European Patent EP 584365. Said plant extracts are, for example, grape seed, *ginseng*, jojoba, kola, lavender, *swertia*, guarana or saw palmetto.
iv) Other remedies, which possess a low efficacy or cause high side effects, are spironolactone, acetylcholine derivatives, estradiol, nicotinic acid amide, nicotinic acid, benzyl nicotinate, glycyrrhizinic acid, cyclosporin and prostaglandin analogues.
v) Unproven treatments are those with Vitamin E, Vitamin B6, biotin, pantothenic acid, amino acids such as arginine, capronium chloride, hinokitiol, serine and methionine, organic acids or oils.

Thus, an effective treatment of hair loss is required. The treatment should be effective at least as minoxidil, without having inherent hypotensive properties and be available for women as well. Preferably, the ideal treatment should not inflict the psychological effect of long-term drug ingestion or induce low patient compliance due to long-term use.

It has been discovered that the use of the mixture of extracts of saw palmetto and *swertia*, derivatives thereof and of components being part of said extracts causes a surprising and unexpected synergistic effect on hair growth, even at minimal concentrations.

The present invention thus consists in a composition comprising a mixture of extracts of saw palmetto and *swertia*, derivatives thereof and of components being part of said extracts.

The composition according to the present invention comprises advantageously the saw palmetto extract, from 0.01–100.0%, preferably between 0.1–50%, more preferably between 1.0–25% and optimally between 2.5–25% by weight; and the *swertia* extract in a concentration from 0.001–20.0%, preferably between 0.1–20%, more preferably between 0.2–5% and optimally between 0.25–2% by weight.

The composition according to the present invention may be topically applied as such or internally ingested within a suitable carrier, solvent, dissolvent, emulgent, extract, solutions e.g. aqueous, alcoholic, oily, suspension; microemulsion, microcapsules, vesicles, etc.

The active agents may be formulated into various compositions, e.g. a lotion, a conditioner, a hair tonic, a shampoo, a lotion with conditioner, a gel, a styling gel, a mousse, a styling wax, a mask, an aerosol, a moisturizer, a powder, a perfume, a brilliantine, a pomade, a dye, a cream or an ointment.

The composition according to the present invention might be formulated as well as an internally ingested tablet, capsule, drops or suspension.

The above composition can be used alone or in conjunction with:
1. Irritating agents, e.g. anthralin, retinol (Vitamin A) and its derivatives, alpha-hydroxy acids, beta-hydroxy acids;
2. Extracts known for their hair revitalizing effect, e.g. *aloe vera*, borage, chamomile, forsynthia, *ginseng*, grape seed, guarana, jojoba, kola, lavender, nettle root, rosemary, pumpkin seed, *polygonum*(Fo-Ti), *pygeum*, red clover, soy, tea tree oil and thyme,
3. Hair nourishment agents, such as vitamins, e.g. tocopherol (Vitamin E) and derivatives, Vitamin B6, biotin, pantothenic acid, Vitamin D and its derivatives, Vitamin C; amino acids e.g. arginine, citrulline, ornithine, serine and methionine; organic acids, e.g. lactate or malate, minerals and metals, e.g. zinc and its derivatives, magnesium, aluminum, death sea minerals; eugenol, polyamines and antioxidants;
4. Low efficacy compounds such as spironolactone, acetylcholine derivatives, estradiol, nicotinic acid amide, nicotinic acid, benzyl nicotinate, cyclosporin, prostaglandin analogues; glycyrrhizic acid and derivatives thereof;
5. Antidandruff anti proliferatives compounds, e.g. zinc pyrithione, coal tar, selenium and its derivatives;
6. Antifungals, e.g. ciclopyroxolamine, piroctone olamine, imidazoles (e.g. ketoconazole, bifonazole), metronidazole, undecylenic acid and derivatives of the said compounds;
7. Antimicrobials, e.g. aluminium chloride, chlorothymol, hexamine, zinc salyci late, zinc sulphide, triclorocarban, triclosan;
8. Anti-inflammatory agents, e.g. bisabolol, panthenol or cyclo-oxygenase inhibi tors;
9. Steroids, e.g. medicated low (hydrocortisone), intermediate (mometasone) thigh (betamethasone, dexamethasone) potency steroids, of plant origin, e.g. phytosterols;
10. Lipid derivatives, e.g. mineral oil, vegetable oil, animal, synthetic oil, fatty alcohol, saturated and unsaturated fatty acids, waxes and squalene;

11. Refrigerants, e.g. menthols;
12. Vasodilating compounds or nitric oxide donors, e.g. of natural source (arginine) or medicated (nitroprusside); and
13. Finasteride or Minoxidil or an 5 alpha reductase inhibitor. The amounts of said derivatives may be varied in accordance with the specific requirements.

The composition according to the present invention may be prepared by conventional methods as becomes apparent from the Experiments given hereinafter.

The present invention also consists in the use of the composition according to the present invention in the preparation of a medicament for the treatment of humans and animals against loss of hair.

The present invention consists also in a method for the treatment for the treatment of humans and animals against loss of hair with a composition according to the present invention.

Data was objectively assessed by the experiments given hereafter in an already established hair growth model in mice [Inaoka Y, et al. 1994, 42:530–3.], employing treatment versus controls. As a positive control, minoxidil 5% was used. Each extract did not affect the hair growth when used alone in our model. However, when both compounds were combined, an increase of hair growth of about 70% beyond baseline was quantified, a result alike that of minoxidil 5%. The present invention thus fulfills the need for a natural combination of plant extracts and provides the advantages of unanimous use and excellent efficacy.

In mice, the hair growth and effluvium are a continuous cyclic process. It was demonstrated that hair growth temporarily ceases at about 7 weeks-old, for about 50 days. Therefore, any hair growth during this period is non-physiologic and induced by external agents. Pharmacological agents applied during this stage, such as minoxidil or retinoids, were shown to induce hair growth (Bazanno, 1993). Any research related to this model should employ minoxidil as the "golden standard" and as an essential positive control.

Mice (males, C3H type), which were in the resting phase in their hair cycle, i.e. at 7 weeks of age, were employed in these experiments. The skin of the back of the mice was subjected to a complete hair cut by an electric razor, with areas of approximately 2.5×4 cm. Different solutions, as will be further described, (100 µL/day) were applied with a syringe 6 times a week for 18 days, and the skin was further massaged. At the end of the experiment, the animals were sacrificed and the skin of the back was excised. The excised skin was fixed on frame consisting of a metal disc with a radius of 0.9 cm. Hairs were cut by a scalpel, collected and weighted.

All formulations contained active ingredients (g/weight) as specified, 20% ethanol and aqua distillata ad 100.0. Minoxidil was used as supplied by the manufacturer (Pharmacia-Upjohn).

i. Control (placebo-treatment)
ii. Positive control—minoxidil 5% (Pharmacia-Upjohn)
iii. Saw Palmetto extract—7.5%
iv. Swertia extract—1%
v. Saw Palmetto —7.5% and Swertia 1% extracts
vi. Saw Palmetto —7.5% and Guarana 10% extracts When synergism has to be demonstrated, one has to use low concentrations of an expected active ingredient and show that each single agent application causes a modest effect, preferably none. In spite of this, the combination of non-active agents should exert a convincible positive result.

The results of said experiments are shown in Table I and FIG. 1 (data not shown in FIG. 1 for group vi).

Table I shows the weighting results in miligrams, which reflect the hair growth in mice during a physiological resting phase of their hair cycle, i.e. without any expected hair growth.

TABLE 1

Figure 1:
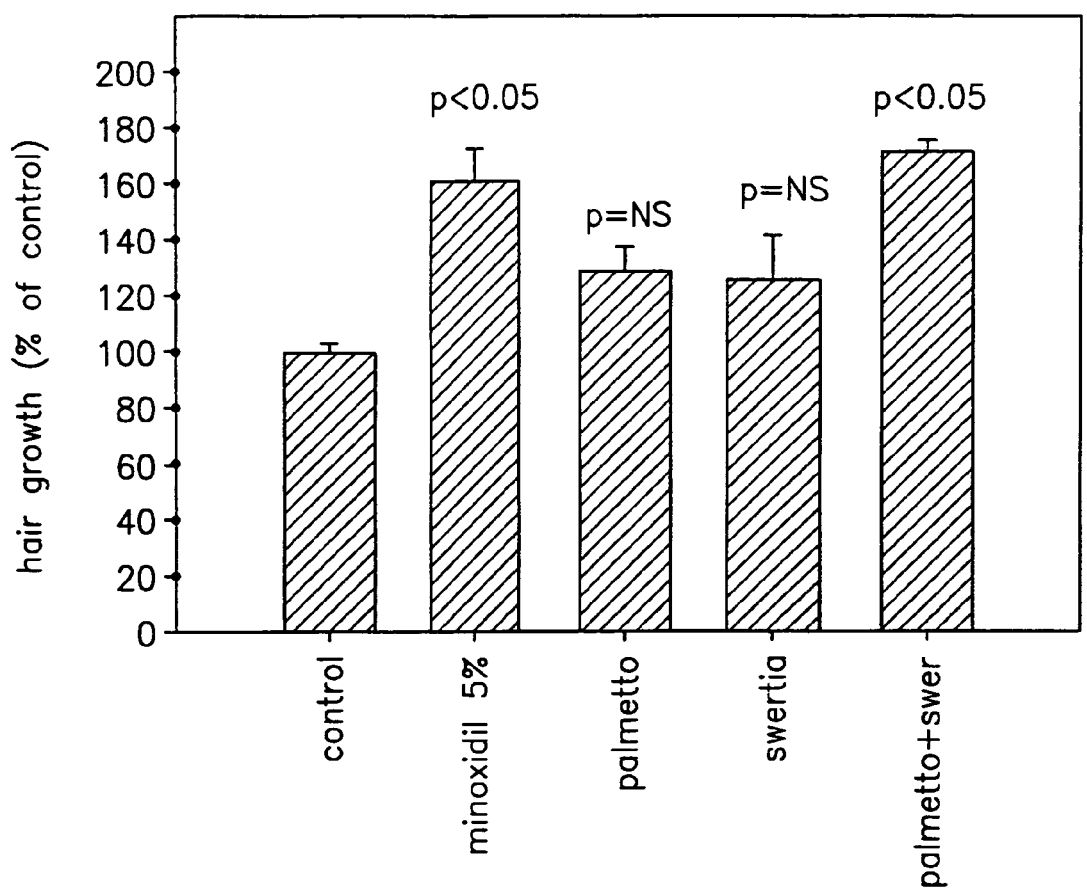
FIG. 1 summarizes the stimulation of hair growth. Data represents hair weight and is given as percentages in comparison to control treatments. Controls and groups ii–v were treated by massaging the back of mice with 20% ethanol in aqua distillata, or 20% ethanol in aqua distillata and active ingredients, correspondingly.

| Treatment | Weight Of Hair (mg) | Standard Error of the Mean | P |
| --- | --- | --- | --- |
| Control (placebo) | 2.52 | 0.08 | |
| Minoxidil 5.0% | 4.07 | 0.44 | P < 0.05 |
| Palmetto 7.5% | 3.26 | 0.25 | P = NS |
| Swertia 1.0% | 3.17 | 0.49 | P = NS |
| Palmetto 7.5% and Swertia 1.0% | 4.34 | 0.16 | P < 0.05 |
| Palmetto 7.5% and Guarana 10.0% | 3.02 | 0.25 | P = NS |

Statistical evaluation by Kruskal-Wallis One Way Analysis of Variance on Ranks. The differences in the median values among the treatment groups are greater than would be expected by chance; there is a statistically significant difference ($p=0.011$) To isolate the group or groups that differ from the others a multiple comparison procedure versus Control Group was used (Dunn's Method). Data was calculated by SigmaStat version 2.0, Jandel.

The Data in both Table 1 and in FIG. 1 are represented as percentages in comparison to control placebo-treated mice. The hair growth stimulation is demonstrated as compared to control of each group, in percentages as follows:

1. The validity of the experimental setup is demonstrated by comparison with a golden standard of minoxidil 5% which effects an increase of hair weight of about 65% as compared to control mice ($p<0.05$).
2. It is demonstrated that palmetto extract 7.5% did not cause an increase of hair growth (p=non significant, NS)
3. It is demonstrated that *swertia* extract 1% did not caused an increase of hair growth (p=NS)
4. However, the combination of extracts at concentrations of *swertia* 1% and palmetto 7.5% resulted in an increase of hair weight of 70% as compared to control mice ($p<0.05$)
5. A combination of palmetto 7.5% and guarana 10% extracts (negative control) did not cause an increase of hair weight (p=NS).

It is concluded that treatment of group v with a combination of saw palmetto extract and *swertia* extract unexpectedly increase hair growth. The synergism is unequivocally specific for saw palmetto and *swertia* extracts, since combination of saw palmetto with another allegedly hair-stimulating extract at a low concentration, i.e. guarana, did not result in synergism (negative control). The synergistic effects of saw palmetto/*swertia* combination reflect a pharmacologically-induced unexpected stimulation of hair growth.

The present invention will now be illustrated with reference to the following Examples without being limited by them.

EXAMPLE 1

Hair Tonic Solution

| INGREDIENT Phase I | % w/w | FUNCTION |
|---|---|---|
| AQUA | 69.0 | |
| ALCOHOL | 20.0 | Solvent, preservative |
| SAW PALMETTO EXTRACT | 10.0 | Active ingredient |
| SWERTIA EXTRACT | 1.0 | Active ingredient |

Manufacturing procedure:

Mix all the components at room temperature.

EXAMPLE 2

Hair Clear Lotion

| INGREDIENT Phase I | % w/w | FUNCTION |
|---|---|---|
| AQUA | 70.0 | |
| ALCOHOL | 20.0 | Solvent, preservative |
| SAW PALMETTO EXTRACT | 7.5 | Active ingredient |
| SWERTIA EXTRACT | 2.0 | Active ingredient |
| Phase II | | |
| PERFUME | 0.2 | Fragrance |
| PEG-40 HYDROGENATED CASTOR OIL (and) POLYSORBATE 20 (and) OCTOXYNOL-11 | 0.3 | Solubilizer |

Manufacturing Procedure:

Mix all the components of the phase I at room temperature.

Mix well the components of the phase II before adding on the phase I.

EXAMPLE 3

Hair Lotion with Conditioner

| INGREDIENT | % w/w | FUNCTION |
|---|---|---|
| ALCOHOL | 39.0 | Solvent, preservative |
| POLYQUATERNIUM-2 | 1.5 | Conditioner |
| HYDROXYPROPYL GUAR HYDROXYPROPYLTRIMONIUM CHLORIDE | 0.3 | Conditioner |
| DIMETHICONE COPOLYOL | 1.0 | Silicone surfactant |
| SAW PALMETTO EXTRACT | 10.0 | Active ingredient |
| SWERTIA EXTRACT | 2.0 | Active ingredient |
| PERFUME | 0.2 | Fragrance |
| AQUA | 46.0 | |

Manufacturing procedure:

Disperse the conditioner in the blend of water and polyquaternium—2.

Add the alcohol, silicone, the extracts I and II and the fragrance. Mix to homogenous. Adjust the pH to 5–5.5

EXAMPLE 4

Hair Gel

| INGREDIENT | % w/w | FUNCTION |
|---|---|---|
| Phase I | | |
| LAURYL GLUCOSIDE | 4.0 | Film former |
| HYDROLYZED COLLAGEN | 1.5 | Film former |
| 1,2-PROPYLENGLYCOLE | 3.0 | Moisturizer |
| PEG-40 HYDROGENATED CASTOR OIL | 2.0 | Solubilizer |
| SAW PALMETTO EXTRACT | 15.0 | Active ingredient |
| SWERTIA EXTRACT | 1.0 | Active ingredient |
| PHENOXYETHANOL (and) METHYL PARABEN (and) ETHYL PARABEN (and) PROPYL PARABEN | 0.3 | Preservative |
| Phase II | | |
| NaOH (10% water sol.) | 3.0 | Neutralizing agent |
| EDTA tetra sodium | 0.2 | Chelating agent |
| AQUA | 14.8 | |
| CARBOMER (Carbopol 980) 2% swelling | 55.0 | Gel former |
| PERFUME | 0.2 | Fragrance |

Manufacturing Procedure:

Mix the ingredients of the phase I, in the listed order at room temperature.

Prepare the base gel of the phase II in the given order and add the phase I.

Mix until homogenous and adjust the pH to 5–5.6 with NaOH sol.

EXAMPLE 5

Hair Styling Gel

| INGREDIENT | % w/w | FUNCTION |
|---|---|---|
| Phase I | | |
| POLYVINYL PIROLIDONE (PVP K-30) | 2.0 | Film former |
| AQUA | 20.0 | |
| Phase II | | |
| ACRYLATE COPOLYMER (Capigel 98) | 1.4 | Gel former |
| AQUA | 10.0 | |
| Phase III | | |
| PEG-40 HYDROGENATED CASTOR OIL (and) POLYSORBATE 20 (and) OCTOXYNOL-11 | 0.3 | Solubilizer |
| SAW PALMETTO EXTRACT | 20.0 | Active ingredient |
| SWERTIA EXTRACT | 2.0 | Active ingredient |
| PERFUME | 0.2 | Fragrance |
| Phase IV | | |
| TRIETHANOLAMIN up to pH = 7.5 | Qs | Neutralizer agent |
| PHENOXYETHANOL (and) METHYL PARABEN (and) ETHYL PARABEN (and) PROPYL PARABEN (and) BUTYL PARABEN | 0.3 | Preservative |
| AQUA | Up to 100.0 | |

Manufacturing Procedure:

Disperse the PVP in the water (phase I).

Dilute the Capigel in the water (phase II).

Dissolved the perfume and the Extracts in the solubilizer (phase III).

Add Phase I to Phase II. Neutralize the gel with triethanolamin than introduce the preservative and the Phase Ill. Adjust the final pH to the optimal range 7.2–7.5.

Add water up to 100.0

EXAMPLE 6

Hair Styling Mousse

| INGREDIENT | % w/w | FUNCTION |
|---|---|---|
| Phase I | | |
| CHITOSAN (Hydagen HCMF) | 0.5 | Styling agent |
| GLYCOLIC ACID | 0.2 | Solubilizer |
| AQUA | 78.5 | |
| Phase II | | |
| POLYVYNIL PYROLIDONE/VINYL ACETATE COPOLYMER (PVP/VA 60:40) | 5.0 | Gelling agent |
| CETRIMONIUM CHLORIDE | 1.0 | Preservative |
| HYDROLYZED WHEAT GLUTEN HYDROLYZED WHEAT PROTEIN | 3.0 | Film former |
| SAW PALMETTO EXTRACT | 10.0 | Active ingredient |
| SWERTIA EXTRACT | 1.5 | Active ingredient |
| PERFUME | 0.3 | Fragrance |

Manufacturing Procedure:

Add and mix the components listed under phase I till is homogenous.

Add ingredients of phase II one by one and keep the pH-value bellow 6.

Adjust the pH value to 4.0.

EXAMPLE 7

Hair Styling Wax

| INGREDIENT | % w/w | FUNCTION |
|---|---|---|
| Phase I | | |
| GLYCERYL STEARATE | 5.0 | Thickener |
| CETEARETH-12 | 1.0 | Emulsifier o/w |
| DECYL OLEATE | 5.0 | Emollient |
| PARAFFIN OIL | 10.0 | Emollient |
| Phase II | | |
| CHITOSAN | 0.8 | Styling agent |
| GLYCOLIC ACID | 0.4 | Solubilizer |
| AQUA | 53.7 | |
| Phase III | | |
| SAW PALMETTO EXTRACT | 20.0 | Active ingredient |
| SWERTIA EXTRACT | 1.5 | Active ingredient |
| CETRIMONIUM CHLORIDE 40% | 2.5 | Preservative |
| PERFUME | 0.1 | Fragrance |

Manufacturing Procedure:

Heat the ingredients listed under phase I at 80–85° C. and mix to homogenous. Mix the ingredients listed under phase II at room temperature till a homogenous solution is obtained. Heat the solution to 80–850° C. and add to the phase I under continuous stirring.

Cool down the emulsion to approx. 50–55° C. and add the ingredient of the phase III. Fill up hot in the commercial package.

REFERENCES CITED

Patents

U.S. Pat. No. 4,596,812, 6/1986, Chidsey, et al,
U.S. Pat. No. 4,760,071, 7/1988, Rasmusson, et al.
U.S. Pat. No. 5,750,107, 5/1998, Nomura, et al.
U.S. Pat. No. 4,769,231, 9/1988, Ogura, et al.
EP 584365, 3/1994, Murayama Articles Bazzano G, et al. Effect of retinoids on follicular cells. J Invest Dermatol 1993 Jul 101:1 Suppl $138s^{-142}S$ Inaoka Y, et al., Studies on active substances in herbs used for hair treatment. Chem Pharm Bull (Tokyo). 1994, Mar;42(3):530 –3.

Koperski et al, Topical minoxidil therapy for androgenetic alopecia. A 30-month study. Arch Dermatol 1987 Nov 123:11 1483–7

The invention claimed is:

1. A composition for inducing hair growth comprising a mixture of extracts of saw palmetto and *swertia*, or their derivatives, or of active components of said extracts in a concentration from 0.01% to 99.9% saw palmetto extract and a concentration of 0.001% to 20% *swertia* and in an internally ingested form selected from the group consisting of tablet, capsule, drops, and suspension.

2. The composition of claim 1 wherein said mixture further comprises an extract for hair invigoration selected from the group consisting of *aloe vera*, borage, chamomile, forsynthia, *ginseng*, grape seed, guarana, jojoba, kola, lavender, neetle root, *polygonum* (Fo-Ti), rosemary, pumpkin seed, *pygeum*, red clover, soy, tea tree oil and thyme.

3. The composition of claim 1 wherein said mixture further comprises a hair nourishment agent selected from the group consisting of vitamin A, B, C, D, E and zinc and its derivatives.

4. The composition of claim 1 wherein said mixture further comprises an antimicrobial agent.

5. The composition of claim 1 wherein said mixture further comprises a nitric oxide donor.

6. The composition of claim 1 wherein said mixture further comprises a suitable carrier, solvent, emulgent or solution.

7. A method of inducing hair growth in humans or animals comprising treating the human or animal with a mixture of saw palmetto extract and *swertia* extract in a concentration from 0.01% to 99.9% saw palmetto extract and a concentration of 0.001% to 20% *swertia*, and in an internally ingested form selected from the group consisting of tablet, capsule, drops, and suspension.

8. A composition for inducing hair growth comprising a mixture of extracts of saw palmetto and *swertia*, or their derivatives, or of active components of said extracts in a concentration from 1% to 50% saw palmetto extract and a concentration of 0.2% to 5.0% *swertia* extract and in an internally ingested form selected from the group consisting of tablet, capsule, drops, and suspension.

9. The composition of claim 8 wherein said mixture further comprises an extract for hair invigoration selected from the group consisting of *aloe vera*, borage, chamomile, forsynthia, *ginseng*, grape seed, guarana, jojoba, kola, lavender, neetle root, *polygonum* (Fo-Ti), rosemary, pumpkin seed, *pygeum*, red clover, soy, tea tree oil and thyme.

10. The composition of claim 8 wherein said mixture further comprises a hair nourishment agent selected from the group consisting of vitamin A, B, C, D, E and zinc and its derivatives.

11. The composition of claim 8 wherein said mixture further comprises an antimicrobial agent.

12. The composition of claim 8 wherein said mixture further comprises a nitric oxide donor.

13. The composition of claim 8 wherein said mixture further comprises a suitable carrier, solvent, emulgent or solution.

14. A composition for inducing hair growth comprising a mixture of extracts of saw palmetto and *swertia*, or their derivatives, or of active components of said extracts in a concentration from 5.0% to 25% saw palmetto extract and a concentration of 0.5% to 2.0% *swertia* extract and in an internally ingested form selected from the group consisting of tablet, capsule, drops, and suspension.

15. The composition of claim 14 wherein said mixture further comprises an extract for hair invigoration selected from the group consisting of *aloe vera*, borage, chamomile, forsynthia, *ginseng*, grape seed, guarana, jojoba, kola, lavender, neetle root, *polygonum* (Fo-Ti), rosemary, pumpkin seed, *pygeum*, red clover, soy, tea tree oil and thyme.

16. The composition of claim 14 wherein said mixture further comprises a hair nourishment agent selected from the group consisting of vitamin A, B, C, D, E and zinc and its derivatives.

17. The composition of claim 14 wherein said mixture further comprises an antimicrobial agent.

18. The composition of claim 14 wherein said mixture further comprises a nitric oxide donor.

19. The composition of claim 14 wherein said mixture further comprises a suitable carrier, solvent, emulgent or solution.

* * * * *